US007005559B1

(12) United States Patent  
Sela et al.

(10) Patent No.: US 7,005,559 B1  
(45) Date of Patent: Feb. 28, 2006

(54) EXPRESSION SILENCING SYSTEM AND DIFFERENT USES THEREOF

(75) Inventors: Ilan Sela, Nes Ziona (IL); Sylvia Zeitoune-Simovich, Tel Aviv (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 09/889,821

(22) PCT Filed: Jan. 16, 2000

(86) PCT No.: PCT/IL00/00029

§ 371 (c)(1),  
(2), (4) Date: Dec. 3, 2001

(87) PCT Pub. No.: WO00/42206

PCT Pub. Date: Jul. 20, 2000

(30) Foreign Application Priority Data

Jan. 18, 1999 (IL) .................................... 128111

(51) Int. Cl.  
*C12N 15/82* (2006.01)  
*C12N 15/90* (2006.01)  
*A01H 1/00* (2006.01)

(52) U.S. Cl. ...................................... 800/285; 800/260

(58) Field of Classification Search ............. 435/320.1; 800/278, 288, 260, 285, 286  
See application file for complete search history.

(56) References Cited

U.S. PATENT DOCUMENTS

| 5,545,817 A | 8/1996 | McBride et al. ............ 800/278 |
| 5,659,124 A | 8/1997 | Crossland et al. .......... 435/468 |

FOREIGN PATENT DOCUMENTS

| WO | WO9727295 | 7/1997 |
| WO | WO9834951 | 8/1998 |
| WO | WO9836083 | 8/1998 |
| WO | WO9853083 | 11/1998 |

OTHER PUBLICATIONS

Blokland et al., Plant J., 1994, vol. 6, pp. 861-877.*  
Palauqui et al., EMBO J., 1997, vol. 16, pp. 4738-4745.*  
Kim et al., Plant Mol. Biol., 1994, vol. 24, pp. 105-117.*  
Alexander et al., J. Virol., 1992, vol., 66, pp. 2934-2942.*  
An, G. (1987) "Binary Ti Vectors for Plant Transformation and Promoter Analysis" *Methods Enzymol* 153: 292-305 (Exhibit 7).  
Baulcombe, D.C. et al. (1996) "Ectopic Pairing of Homologous DNA and Post-Transcriptional Gene Silencing in Transgenic Plants" *Curr. Opin. Biotechnol.* 7:173-180 (Exhibit 8).

Boerjan, W. et al. (1994) "Distinct Phenotypes Generated by Overexpression and Suppression of S-Adenosyl-L-Methionine Synthetase Reveal Developmental Patterns of Gene Silencing in Tabacco" *Plant Cell* 6:1401-1414 (Exhibit 9).  
Caviedes, M.A. et al. (1994) "T7 RNA Polymerase is Expressed in Plants in a Nicked But Active Form" *The 4th Intl. Congress of Plant Mol. Biol.* Abstract #479 (Exhibit 10).  
Chamberlin, M. et al. (1982) "Bacteriophage DNA-Dependent RNA Polymerases" in 15 *The Enzymers* 87-108 (Boyer P.D. ed., Academic Press) (Exhibit 11).  
De Carvalho-Niebal, F. et al. (1995) "Post-Transcriptional Cosuppression of β-1,3-Glucanase Genes Does Not Affect Accumulation of Transgene Nuclear mRNA" *Plant Cell* 7:347-358 (Exhibit 13).  
Depicker, A. et al. (1997) "Post-transcriptional Gene Silencing in Plants" *Curr. Opin. Cell Biol.* 9:373-382 (Exhibit 14).  
Dunn, J.J. et al. (1983) "Complete Nucleotide Sequence of Bacteriophage T7 DNA and the Locations of T7 Genetic Elements" *J. Mol. Biol.* 166:477-535 (Exhibit 15).  
Dunn, J.J. et al. (1988) "Targeting Bacteriophage T7 RNA Polymerase to the Mammalian Cell Nucleus" *Gene* 68:259-266 (Exhibit 16).  
Flavell, R.B. et al. (1994) "Inactivation of Gene Expression in Plants as a Consequence of Specific Sequence Duplication" *Proc. Natl. Acad. Sci. USA* 91:3490-3496 (Exhibit 17).  
Fuerst, T.R. et al. (1987) "Use of a Hybrid Vaccinia Virus-T7 RNA Polymerase System for Expression of Target Genes" *Mol. Cell. Biol.* 7:2538-2544 (Exhibit 18).  
Fuerst, T.R. et al. (1986) "Eukaryotic Transient-Expression System Based on Recombinant Vaccinia Virus That Synthesizes Bacteriophage T7 RNA Polymerase" *Proc. Natl. Acad. Sci. USA* 83:8122-8126 (Exhibit 19).  
Gallie, D.R. et al. (1987) "The 5'-leader Sequence of Tobacco Mosaic Virus RNA Enhances the Expression of Foreign Gene Transcripts In Vitro and In Vivo" *Nucleic Acids Research* 15:3257-3273 (Exhibit 20).

(Continued)

*Primary Examiner*—Ashwin Mehta  
(74) *Attorney, Agent, or Firm*—John P. White, Esq.; Cooper & Dunham LLP

(57) ABSTRACT

The invention relates to an expression-silencing system comprising a first DNA construct comprising a nucleotide sequence corresponding to the T7 RNA polymerase gene (T7-pol) which carries an NLS sequence, and at least one promoter and at least one terminator sequence operably linked to the T7-pol; a second DNA construct comprising a T7 promoter sequence (pT7), at least one targeting sequence downstream to said pT7 and at least one 3' non-translated terminator sequence operably linked to the targeting sequences; which system can, upon its introduction into a cell, substantially silence the expression at the RNA level of a target sequence in the cell, in a tissue or organ regenerated from said cell, or in a progeny thereof, substantially silenced, by causing the substantial disappearance of the RNA or RNA transcript carrying said sequence or a functional part thereof.

10 Claims, 3 Drawing Sheets

OTHER PUBLICATIONS

Goodwin, J. et al. (1996) "Genetic and Biochemical Dissection of Transgenic RNA-Mediated Virus Resistance" *Plant Cell* 8:95-105 (Exhibit 21).

Jefferson, R.A. (1987) "Assaying Chimeric Genes in Plants: The GUS Gene Fusion System" *Plant Mol. Biol. Rep.* 5:387-405 (Exhibit 22).

Lassner, M.W. et al. (1991) "Targeting of T7 RNA Polymerase to Tobacco Nuclei Mediated by an SV40 Nuclear Location Signal" *Plant Mol. Biol.* 17:229-234 (Exhibit 23).

Lin, C.H. et al. (1997) "Optimization of Electroporation Conditions for Expression of GUS Activity in Electroporated Protoplasts and Intact Plant Cells" *Plant Physiol. Biochem.* 35:959-968 (Exhibit 24).

Lieber, A. et al. (1989) "High Level Gene Expression in Mammalian Cells by a Nuclear T7-Phage RNA Polymerase" *Nucleic Acids Research* 17:8485-8493 (Exhibit 25).

Lindbo, J.A. et al. (1993) "Induction of a Highly Specific Antiviral State in Transgenic Plants: Implications for Regulation of Gene Expression and Virus Resistance" *Plant Cell* 5:1749-1759 (Exhibit 26).

Matzke, M.A. et al. (1994) "Inactivation of Repeated Genes-DNA-DNA Interaction?" in *Homologous Recombination and Gene Silencing in Plants* 271-307 (J. Paszkowski ed., Kluwer Academic Publishers) (Exhibit 27).

Matzke, M.A. (1990) "Gene Interactions and Epigenetic Variation in Transgenic Plants" *Dev. Genet.* 11:214-223 (Exhibit 28).

Matzke, M.A. et al. (1989) "Reversible Methylation and Inactivation of Marker Genes in Sequentially Transformed Tobacco Plants" *EMBO J.* 8:643:649 (Exhibit 29).

Matzke, M.A. et al. (1993) "A Variety of Epistatic Interactions Can Occur Between Partially Homologous Transgene Loci Brought Together by Sexual Crossing" *Mol. Gen. Genet.* 236:379-386 (Exhibit 30).

McBride, K.E. et al. (1994) "Controlled Expression of Plastid Transgenes in Plants Based on a Nuclear DNA-encoded and Plastid-targeted T7 RNA Polymerase" *Proc. Natl. Acad. Sci. USA* 91:7301-7305 (Exhibit 31).

Metzlaff, M. et al. (1997) "RNA-Medicated RNA Degradation and Chaleone Synthase a Silencing in Petunia" *Cell* 88:845-854 (Exhibit 32).

Meyer, P. et al. (1996) "Homology-Dependent Gene Silencing In Plants" *Annu. Rev. Plant Physiol. Plant Mol. Biol.* 47:23-48 (Exhibit 33).

Moffatt. B.A. et al, (1984) "Nucleotide Sequence of the Gene for Bacteriophage T7 RNA Polymerase" *J. Mol. Biol.* 173:265-269 (Exhibit 34).

Montgomery, M.K. et al. (1998) "Doubled-stranded RNA as a Mediator in Sequence-Specific Genetic Silencing and Co-supression" *Trends in Genetics* 14:255-258 (Exhibit 35).

Moss, B, et al. (1990) "New Mammalian Expression Vectors" *Nature* 348:91-92 (Exhibit 36).

Mueller, E. et al. (1995) "Homology-dependent Resistance: Transgenic Virus Resistance in Plants Related to Homology-dependent Gene Silencing" *Plant J.* 7:1001-1013 (Exhibit 37).

Murashige, T. et al. (1962) "A Revised Medium for Rapid Growth and Bio Assays with Tabacco Tissue Cultures" *Physiol. Plant.* 15:473-497 (Exhibit 38).

Napoli, C. et al. (1990) "Introduction of a Chimeric Chalcone Synthase Gene into Petunia Results in Reversible Co-Suppression of Homologous Genes in trans" *Plant Cell* 2:279-289.

Smith, C.J.S. et al. (1990) "Expression of a Truncated Tomato Polygalacturonase Gene Inhibits Expression of the Endogenous Gene in Transgenic Plants" *Mol. Gen. Genet.* 224:477-481 (Exhibit 40).

Stam, M. et al. (1997) "The Silence of Genes in Transgenic Plants" *Ann. Bot.* 79:3-12 (Exhibit 41).

Studier, F.W. et al. (1986) "Use of Bacteriophage T7 RNA Polymerase to Direct Selective High-level Expression of Cloned Gene" *J. Mol. Biol.* 189:113-130 (Exhibit 42).

Tabor, S. et al. (1985) "A Bacteriophage T7 RNA Polymerase/Promoter System for Controlled Exclusive Expression of Specific Genes" *Proc. Natl. Acad. Sci. USA* 82:1074-1078 (Exhibit 43).

Tanzer, M.M. et al. (1997) "Characterization of Post-Transcriptionally Suppressed Transgene Expression That Confers Resistance to Tobacco Etch Virus Infection in Tobacco" *Plant Cell* 9:1411-1423 (Exhibit 44).

Tuttle, A. et al. (1994) "Expression of T7 Transcripts in Plant Cells By Bacteriophage T7 RNA Polymerase" *The 4th Intl. Congress of Plant Mol. Biol.* Abstract#478 (Exhibit 45).

Van Blockland R. et al. (1994) "Transgene-mediated Suppression of Chalcone Synthase Expression in *Petunia hybrida* Results from an Increase in RNA Turnover" *Plant J.* 6:861-877 (Exhibit 46).

Vardi, E. et al. (1993) "Plants Transformed with a Cistron of a Potato Virus Y Protease (NIa) are Resistant to Virus Infection" *Proc. Natl. Acad. Sci. USA* 90:7513-7517 (Exhibit 47).

Weschke, W. et al. (1994) "T7 RNA Polymerase Mediated Expression in Transgenic *N. Tabaccum* Plants" *The 4th Intl. Congress of Plant Mol. Biol.* Abstract #480 (Exhibit 48); and.

Zeitoune, S. et al. (1999) "T7 RNA Polymerase Drives Transcription of a Reporter Gene from T7 Promoter, But Engenders Post-Transcriptional Silencing of Expression" *Plant Science* 141:59-65 (Exhibit 49).

Cox, K.H. et al. (1988) "Analysis of Plant Gene Expression" in *Plant Molecular Biology, A Practical Approach* (Shaw, C.H. ed., IRL Press), pp. 1-35 (Exhibit 1).

\* cited by examiner

EXPRESSION SILENCING SYSTEM AND DIFFERENT USES THEREOF

FIELD OF THE INVENTION

The present invention relates to an expression-silencing system which is capable, upon introduction thereof into a selected cell, of rendering the expression, at the RNA level, of a target sequence in said cell, in a tissue or organ regenerated therefrom or in a progeny thereof, substantially silenced. The invention also concerns the different uses of the expression-silencing system of the invention.

BACKGROUND OF THE INVENTION

There have been some attempts by scientists to increase expression levels of transgenes in transgenic animals and plants by the introduction of a bacteriophageT7 polymerase/T7 promoter (T7-pol/pT7) system thereinto. T7 RNA polymerase (T7-pol) is a single polypeptide of ~98 kDa which specifically recognized the short viral promoter pT7 [Dunn J. J. et al., J. Mol. Biol. 166:477–535 (1983); Moffatt B. A. et al. J. Mol. Biol. 173:265–269 (1984)]. T7-pol does not require auxiliary proteins for transcription [Chamberlin M., and Ryan T. The Enzymes Ed. Boyer P. D. Academic Press N.Y 15:87–108 (1982)] and recognizes a single (albeit nor stringent) terminator.

It was suggested that any gene placed under the control of the T7 promoter will be specifically and strongly transcribed by a cloned T7 RNA polymerase, which was proven to be successful in bacteria [Tabor S., and Richardson C., Proc. Natl. Acad. Sci USA 82:1074–1078 (1985); Studier F. W., and Moffatt, B. A., J. Mol. Biol. 189:113–130 (1986)], and somewhat successful in animal cells [Fuerst T. R., et al. Proc. Natl. Acad. Sci. USA 83:8122–8126 (1986); Fuerest T. R., et al. Mol. Cell. Biol. 7:2538–2544 (1987)] Dunn J. J., et al. Gene 68:259–266 (1988); Lieber, A., et al. Nucl. Acids Res. 17:8485–8493 (1989); M ss, B., et al. Nature 348: 91–92 (1990)].

The situation in plants is more vague. The expression of T7-pol in tobacco protoplasts and the NLS-direction of the expressed enzyme to the nucleus has been reported [Lassner M. W. et al. Plant Mol. Biol. 17:229–234 (1991)]. In addition, the expression of either T7-pol or a reporter gene driven by the T7-pol/pT7 system in plants was described [Caviedes, M. A., et al., Abstract #479 of the 4$^{th}$ Intl Congress of Plant Mol. Biol (1994); Tuttle A., et al. Abstract #478 of the 4$^{th}$ Intl Congress of Plant Mol. Biol (1994)]. A more successful T7-pol/pT7 expression system was described [Tuttle, A. et al. Abstracts of the 4$^{th}$ Int. Congress of Plant Mol Biol #478 (1994)] in which T7-pol expressed in tobacco but targeted to the protoplast, directed expression of GUS. A T7-derived system which promotes expression in plants was also described in the course of a novel method to produce hybrid seeds [U.S. Pat. No. 5,659,124] and in plastids which may be considered as prokaryotic cells [McBride, K. E. et al. Proc. Natl. Acad. Sci. USA 91:7301–7305 (1994); U.S. Pat. No. 5,545,817].

Gene silencing in transgenic plants is a documented phenomenon, which relates to the introduction of a foreign gene into a cell thereby inducing its silencing, rather than its expression [Cox K. H., and Goldberg R. B. in Plant Molecular Biology, A Practical Approach (Shaw, C. H., ed). Washington D.C. IRL Press, IRL Press, pp. 1–35 (1988); Baulcombe D.C., and English J. J., Curr. Opin. Biotechnol. 7:173–180 (1996); Meyer P., and Seedler, H., Annu. Rev. Plant Physiol. Plant Mol. Biol. 47:23–48 (1996); Stam M., et al. Ann. Bot. 79:3–12 (1997)]. In general, the insertion of a particular gene into a plant may cause the silencing of homologous native or transgenic genes, which is referred to as "co-suppression" [Depicker A., et al. Curr. Opin. Cell Biol. 9:373–382 (1997); Matzke M. A., et al. EMBO J. 8:643–649 (1989); Matzke M. A., et al. Mol. Gen. Genet. 238:379–386 (1993); Napoli C., et al. Plant Cell 2:279–289 (1990)]. Co-suppression may also be caused by the introduction of homologous RNAs into the cells, such as viral RNAs [Lindbo J. A., et al. Plant Cell 5:1749–1759 (1993); Mueller E., et al. Plant J. 7:1001–1013 (1995)].

Silencing may occur at the transcriptional level, i.e. inhibition of transcription [Flavell R. B. Proc. Natl. Acad. Sci. USA 91:3490–3496 (1994); Matzke M. A. et al. in Homologous Recombination and Gene Silencing in Plants Ed. Paszkowski J. Kluwer Academic Publishers, Dordrecht 271–307] or post-transcriptionally [Van Blokland R. et al. Plant J. 6:861–877 (1994); B erjan W., et al. Plant Cell 6:1401–1414 (1994); De Carvalho-Niebel F., et al. Plant Cell 7:347–358 (1995)]. It has been suggested that silencing at the post-transcriptional level is caused by degradation of the primary transcript of the expressed gene, thus no mRNA and no protein will be found in the cytoplasm [Tanzer M. M., et al. Plant Cell 9:1411–1423 (1997)]. Furthermore, silencing-triggering mechanism involving the sensing of RNA levels [Goodwin J., et al. Plant Cell 8:95–105 (1996); Smith C. J. S., et al., Mol. Gen. Genet. 224:477–481 (1990); Metzlaff M., et al. Cell 88:845–854 (1997)] or ectopic pairing of homologous DNA sequences [Baulcombe D.C., and English J. J., Curr. Opin. Biotechnol. 7:173–180 (1996); Matzke M. A., Dev. Genet 11:214–223 (1990)] have also been suggested. Plant cells which have been silenced for a certain viral transgen and thus became resistant to virus infection due to the specific degradation of viral sequences have also been described [Lindbo J. A., et al. (1993) ibid.; Goodwin J., et al. (1996) ibid.].

SUMMARY OF THE INVENTION

The present invention relates to an expression-silencing system comprising: (a) a first DNA construct comprising a nucleotide sequence corresponding to the T7 RNA polymerase gene (T7-pol) or to a functional equivalent or fragment thereof, which sequence carries an NLS sequence, the construct further comprising at least one promoter and at least one terminator sequence operably linked to said T7-pol; (b) a second DNA construct comprising a T7 promoter sequence (pT7) or a functional fragment thereof, at least one targeting sequence downstream to said pT7 and at least one 3' non-translated terminator sequence operably linked to said targeting sequence which system is capable, upon introduction thereof into a cell, or rendering the expression at the RNA level of a target sequence in said cell, in a tissue or organ regenerated from said cell, or in a progeny thereof, substantially silenced, by causing the substantial disappearance of the RNA or RNA transcript carrying said sequence or a functional part thereof.

In the same aspect, the invention relates to an expression-silencing system comprising a nucleotide sequence corresponding to the T7 RNA polymerase gene (T7-pol) or a functional equivalent or fragment thereof which sequence carries an NLS sequence, the construct further comprising at least one promoter and at least one terminator sequence operably linked to said T7-pol, a T7 promoter (pT7) or a functional equivalent or fragment thereof, at least one targeting sequence downstream to said the pT7, and at least one additional terminator sequence operably linked to said nucleic acid sequence of interest, said system being capable, upon introduction thereof into a cell, of rendering the expression at the RNA level of a target sequence in said cell, in a tissue or organ regenerated from said cell, or in a progeny thereof, substantially silenced, by causing the substantial disappearance of the RNA or RNA transcript carrying said sequence.

In a second aspect, the invention relates to a process for the transformation of a plant with a gene-silencing system, which process comprises: (a) transforming plant cells with the expression-silencing system of the invention; (b) selecting the plant cells transformed with at least one DNA construct according to (a) and regenerating said selected cells to provide a differentiated flowering plant; and (c) hybridizing a plant transformed with said first DNA construct with a plant transformed with said second DNA construct, which first plant and second plant are obtained in (b), said hybridization thus providing a double-transformed plant in which the expression of a target sequence is substantially suppressed.

Further, the invention relates to a method for producing a transgenic plant carrying a substantially silent target sequence, by hybridizing a plant carrying and expressing said target sequence with a transformed plant obtained by the process of the invention.

Still further, the invention relates to a method for producing a transgenic plant carrying a substantially silent target sequence, by grafting a plant, or parts thereof, carrying and expressing said silent target sequence on a transformed plant obtained by the process of the invention.

Yet further, the invention relates to a method of silencing the expression of a target sequence within the genome of a plant or within the genome of a plant-infecting pathogen, which method comprises the steps of: (a) providing a first plant capable of regenerating; (b) hybridizing said first plant with a second plant transformed with the expression-silencing system of the invention; and (c) selecting those plants obtained by the hybridization of step (b), in which the expression of said target sequence is substantially silenced.

Finally, the invention relates to a method of identifying nucleic acid of interest within the genome of a plant, wherein the nucleic acid of interest encodes a pre-defined plant phenotype, which process comprises the steps of: (a) providing a first plant carrying in its genome said nucleic acid of interest; (b) transforming said first plant or cells thereof with a second plant or cells thereof, respectively, transformed with the expression-silencing system of the invention; (c) selecting from the population obtained in step (a) transformed plants/plant cells in which the pre-defined phenotype is substantially silenced; and (d) employing said random nucleic acid sequence within the genome of transformed plants selected in step (c) as a probe in screening genomic DNA and cDNA libraries of said first plant, thereby identifying the gene comprising said random nucleic acid sequence, which gene is responsible for said pre-defined phenotype.

BRIEF DESCRIPTION OF THE FIGURES

FIG. 1A represents the p35S-GUS construct, FIG. 1B represents the p35S-T7pol construct and FIG. 1C pT7-GUS construct.

This figure represents the Western blot analysis for the expression of T7-pol. Lane 1 indicates protein extract from a non-transformed plant. Lanes 2 to 7 indicate extracts from various double-transformed plants. Lane 8 represents a commercial T7 RNA polymerase.

FIG. 3A–3B Nuclear run-on transcription assay of p35S-GUN and p35S-T7pol/pT7-GUS plants.

FIG. 3A—Transcripts from p35S-GUS nuclei served as a probe. FIG. 3B—Transcripts from p35S-T7pol/pT7-GUS nuclei served as probes. The various membrane "slots" contain plasmids carrying portions of the following cDNA sequence: GUS, the nuclear subunit of rubisco (Rub), actin (Act), NPTII (Km), T7-pol (T7 RNAP), ubiquitin (Ubiq) and the irrelevant plasmid Bluescript (B.S.). Empty slots are indicated by (-).

Figure 4A:
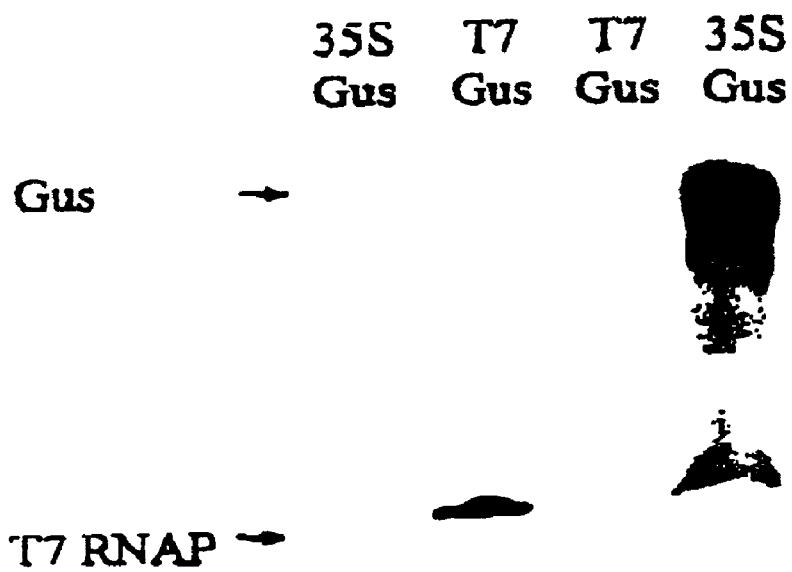
Figure 4B:

FIG. 4A–4B RNase protection assay.

FIG. 4A shows RNase protection assay with a T7-pol probe, presented by the two left lanes and RNase protection with a GUS probe presented by the two right lanes. FIG. 4B shows the RNase protection assay with an actin probe. 35S-GUS designates RNA extracted from p35S-GUS-carrying plants, whereas, T7-GUS designates RNA extracted from plants carrying p35S-T7-pol/pT7-GUS. The arrows indicate the expected positions of GUS, T7-pol and actin.

DETAILED DESCRIPTION OF THE INVENTION

In an attempt to construct a "super-expressing" transgenic plant, by transforming tobacco plants with the T7pol/pT7 system, known to increase expression levels in bacteria and, to some extent, in animal cells, the inventors have surprisingly found that plants transformed with the enzyme T7-pol under the control of the constitutive promoter CaMV-35S (p35S), as well as with a reporter gene (GUS) placed under the control of the pT7, were silenced in respect of GUS expression although sufficiently expressing T7-pol.

Thus, the present invention relates to an expression-silencing system comprising: a first DNA construct comprising a nucleotide sequence corresponding to the T7 RNA polymerase gene (T7-pol) or to a functional equivalent or fragment thereof which sequence carries an NLS sequence, the first construct further comprising at least one promoter and at least one terminator sequence operably linked to the T7-pol; and a second DNA construct comprising a T7 promoter sequence (pT7) or a functional fragment thereof, at least one targeting sequence downstream to said pT7 and at least one 3' non-translated terminator sequence operably linked to the targeting sequence; which system is capable, upon introduction thereof into a cell, of rendering the expression at the RNA level of a target sequence in said cell, in a tissue or organ regenerated from said cell or progenies thereof, substantially silenced, which silencing is caused by the substantial disappearance of the RNA or RNA transcript carrying said sequence or a part thereof.

Alternatively, the expression-silencing system of the invention may comprise a nucleotide sequence corresponding to the T7 RNA polymerase gene (T7-pol) or a functional equivalent or fragment thereof which sequence carries an NLS sequences, the system further comprising at least one promoter and at least one terminator sequence operably linked to said T7-pol, a T7 promoter (pT7) or a functional equivalent or fragment thereof, at least one targeting sequence downstream in the pT7, and at least one additional terminator sequence operably linked to said nucleic acid sequence of interest, said system being capable, upon introduction thereof into a cell, of rendering the expression at the RNA level of a target sequence in said cell, in a tissue or organ regenerated from said cell, or in progenics thereof, substantially silenced, by causing the substantial disappearance of the RNA or of an RNA transcript carrying said sequence.

By the term 'functional equivalent/analogue/fragment thereof' is meant any variant of the nucleic acid sequence which retains the biological function of the peptide, protein or protein product transcribed therefrom or any variant of the protein or peptide itself which retain their biological function. Such variants may include modifications, mutations, deletions replacements and/or insertions within the naturally occurring sequence.

The term 'targeting sequence' for purposes defined herein refers to any exogenous sequence which is introduced into a selected cell by means known to the man of the art, such as by employing the expression-silencing system defined herein. Exogenous nucleic acid sequences according to the invention can possess sequences identical or substantially homologous to an endogenous sequence/s or to a part thereof which endogenous sequence/s are present in the cell prior to introduction of said system into said cell. Yet, the exogenous nucleic acid sequence can possess sequences identical or substantially homologous to a pathogenic nucleic acid sequence present in said cell through infection thereof by a pathogen. Naturally, the expression-silencing system of the invention may contain one or more targeting sequences.

The targeting sequences according to the invention are those which permit integration into the genome of the selected cell containing the target gene of interest or into any other nucleic-acid sequence present in said cell either prior to introduction of the system of the invention into the cell or as a result of a later infection. Such sequences include those encoding a pathogenic product (e.g. a protein or a peptide), irrespective of whether the pathogenic genome will constitute an integral part of the genome of the cells.

The targeting sequences may be a coding or a non-coding nucleic acid sequence either lying upstream of the transcriptional start site, within the primary transcript, or downstream of the transcriptional stop site of the nucleic acid of interest (target sequence), or the targeting sequence may be any sequence present in the cell through a previous modification. Thus, the targeting sequence or sequences according to the invention may, independently, correspond to the sequence within a gene of interest (such as, the sequences of an exon and/or intron), immediately adjacent to a gene of interest (i.e., with no additional nucleotides between the targeting sequence and the coding region of the gene of interest), upstream gene of interest (such as the sequences of the upstream non-coding region or promoter sequences), or upstream of and at a distance from the gene (such as, sequences upstream of the promoter sequences).

By the term 'target sequence' is means any sequence, the suppression of expression of which is desired. The sequence may be endogenous or it may be a sequence of an infecting pathogen. Preferably, the selected cell in which the expression at the RNA level is substantially silenced is any eukaryotic or prokaryotic cell such as a plant cell, a mammalian cell, bacteria, yeast, their pathogens or any suitable tissue culture cells.

By the term 'regenerated tissue or organ' is meant any differentiated tissue or organ regenerated from the cell into which the system of the invention was introduced. One example for a regenerated organ according to the invention is a differentiated flowering plant regenerated from a plant cell into which the silencing system of the invention was introduced.

The silencing of expression by the system of the invention occurs at the RNA level as indicated by the disappearance of the RNA carrying the target sequence, a part thereof or a sequence corresponding thereto. A specific example for such disappearance may be seen in FIGS. 3 and 4, which show that although the GUS gene is transcribed, no GUSmRNA is detected. The RNA according to the invention can be any RNA sequence, either a coding or a non-coding one or it may be a transcript of an RNA or DNA coding or non-coding sequences.

In particular, the target sequence according to the invention corresponds to: (a) a gene encoding a protein or a peptide product, the silencing of which is desired; (b) a non-coding nucleic acid sequence, which, under normal conditions, promotes the expression of an essential coding sequence; (c) a nucleic acid sequence which corresponds to (a) or to (b) or to a fragment thereof, within the scope of degeneracy of the genetic code; or (d) a nucleic acid sequence which hybridizes with the sequence according to (a), to (b), or to (c) or with fragments thereof, which hybridization is carried out under conditions which allow such hybridization to occur. The conditions for hybridization vary and include, for example, hybridization at about 50° C. in a solution containing 0.9 M of a suitable salt, such as NaCl.

In case the selected cell is a plant cell, the target gene may encode an expressible plant protein or peptide or an expressible protein or peptide product of a plant pathogen.

The protein or peptide product of the plant pathogen may be selected from a plant virus, a bacterium or a fungus, all of which are capable of infecting the plant. One example for a target gene encoding a bacterial protein in the GUS gene that may be introduced into to the plant cell by methods known to the man of the art and is then expressed in the plant cell.

Alternatively, the target gene according to the invention may be a gene that encodes a human protein or peptide product or a protein or peptide product of a human pathogen. Accordingly, the system of the invention will render the expression of the human target gene substantially silenced.

Yet further, the target sequence according to the invention may be a non-coding sequence including, inter alia, one or more regulatory elements which, under normal conditions, promotes the expression of a specific coding sequence.

Within the expression-silencing system of the invention, the pT7 corresponds to the promoter region of the bacteriophage T7 or to functional analogues thereof, which promoter is capable of initiating transcription of at least one targeting sequence downstream thereto.

According to one particular embodiment of the invention, the target sequence is the TMV non-coding sequence Ω [Gallie D. R. et al. Nucl. Acids Res. 15:3257–3272 (1987)], the NLS sequence is preferably the SV-40 NLS sequence, the promoter sequence is preferably the plant promoter p35S and the terminator is preferably the NOS terminator. An example for a system consisting of the above elements may be seen in FIG. 1. As an alternative to the NOS terminator, the β-1,3-gluconase terminator may be utilized or any other suitable terminator which is capable of terminating the transcription of a nucleic acid sequence and of the adding polyadenylated ribonucleotides to the 3 end of the primary transcript of the target sequence.

Within one embodiment of the system of the invention, the T7 terminator and the NOS terminator are operably linked within the system of the invention to the targeting sequence. Evidently, any functional equivalent or fragment of the NLS sequence, the promoter or the terminator sequence may be employed in the expression-silencing system of the invention.

Figure 1A:
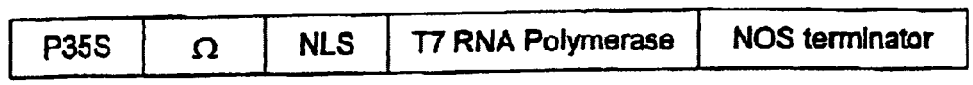
FIG. 1A–1C Schematic representation of the various constructs introduced into plants.
Figure 1B:
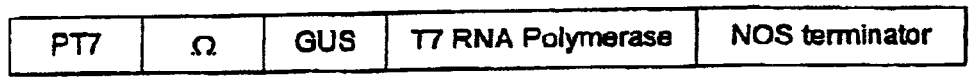

As indicated above, a particular embodiment of the first and second DNA constructs of the invention is shown in FIGS. 1A and 1B, respectively. As may be understood from the figures, the different constituents comprising each construct are linked in a predefined order to enable the efficient silencing of the target gene in the selected cell, upon introduction of the system thereto.

According to a second aspect, the invention relates to a process for the transformation of a plant with a gene-silencing system which process comprises the steps of: (a) transforming plant cells with: (i) a first DNA construct comprising a nucleotide sequence corresponding to the T7 RNA polymerase gene (T7-pol) or a functional equivalent or fragment thereof, at least one plant promoter and at least one plant terminator sequence operably linked to said T7-pol; and with (ii) a second DNA construct comprising a T7 promoter sequence or a functional fragment thereof, a targeting sequence downstream to the T7 promoter, and at least one 3' non-translated terminator sequence operably linked to the targeting sequence, said construct optionally further comprising other additional regulatory elements operably linked to the targeting sequence. The process further comprises the steps of (b) selecting the plant cells transformed with at least one DNA construct according to (a) and regenerating said selected cells to provide a differentiated flowering plant; and (c) hybridizing a plant transformed with said first DNA construct with a plant transformed with said second DNA construct, which first plant and second plant are obtained in (b), the hybridization thus provides a double-transformed plant wherein the expression of a target sequence is substantially suppressed. Evidently, cells transformed with both constructs at a single process stage may be utilized for further hybridizations as described herein after.

Within the same aspect, the invention also concerns to a process for the transformation of plant with a gene-silencing system, which process comprises the steps of: (a) transforming plant cells with a DNA construct comprising a nucleotide sequence corresponding to the T7 RNA polymerase gene (T7-pol) or a functional equivalent or fragment thereof which sequence carries an NLS sequence, the construct further comprising at least one plant promoter sequence and at least one plant terminator sequence operably linked to the polymerase gene, a T7 promoter sequence (pT7) or a functional fragment thereof, a targeting sequence downstream to said pT7, and at least one additional terminator sequence operably linked to said targeting sequence, which DNA construct is capable, upon transformation thereof into a plant, of rendering the expression of a target sequence in said plant or in its progeny, substantially silenced; (b) selecting plant cells transformed with said DNA construct according to (a) and regenerating said selected cells to provide such differentiated flowering plant.

According to this process the targeting sequence substantially corresponds to the target sequence or to a fragment thereof. In addition, the target sequence according to the process disclosed herein corresponds to: (a) a gene encoding a protein or a peptide product, the silencing of which is desired; (b) a non-coding nucleic acid sequence, which, under normal conditions, promote the expression of an essential coding sequence; (c) a nucleic acid sequence which corresponds to (a) or to (b) or to a fragment thereof, within the scope of degeneracy of the genetic code; or (d) a nucleic acid sequence which hybridizes with the sequence according to (a), to (b), or to (c) or with fragments thereof, which hybridization is carried out under conditions which allow such hybridization to occur. Such hybridization conditions vary and include, inter alia, hybridization at 50° C. in a suitable electrolyte, such as NaCl, solution (0.9M).

As may be seen in the following Examples, upon introduction of the expression-silencing system of the invention (FIGS. 1A and 1B), containing as the target gene the sequence encoding the GUS protein, into a plant cell that was previously engineered to express this bacterial protein, the expression of the gene was suppressed.

In a third aspect, the invention relates to a method for producing a transgenic plant carrying a substantially silent target sequence, by hybridizing a plant carrying and expressing said target sequence with a transformed plant obtained by the process of the invention.

In yet another aspect, the invention relates to a method for producing a transgenic plant carrying a substantially silent target sequence, by grafting a plant, or parts thereof, carrying and expressing said silent target sequence on a transformed plant obtained by the process of the invention, as shown in Example 4.

Transgenic plants or progenies thereof obtained by the above disclosed methods, in which the expression of a predefined target sequence is substantially suppressed as the result of said hybridization, are also within the scope of the invention.

In a further aspect, the invention concerns with a method of silencing the expression of a target sequence within the genome of a plant or within the genome of a plant infecting pathogen present in the cell prior to the following manipulations, which method comprises the steps of: (a) providing a first plant capable of regenerating; (b) hybridizing said first plant with a second plant transformed with: (i) a first DNA construct comprising a nucleotide sequence corresponding to the T7 RNA polymerase gene (T7-pol) or a functional equivalent or fragment thereof which sequence carries an NLS sequence, said construct further comprising at least one plant promoter and at least one plant terminator sequence operably lined to said sequence; and with (ii) a second DNA construct comprising a T7 promoter sequence (pT7), a targeting sequence downstream to said pT7 and a 3' non-translated terminator sequence operably linked to said targeting sequence, said construct optionally further comprising additional regulatory elements operably linked to said targeting sequence, said plant being referred to as a double-transformed plant; and (c) selecting plants obtained by the hybridization of step (b), in which the expression of said target sequence is substantially silenced.

Alternatively, the method of silencing the expression of a target sequence within the genome of a plant according to the invention or with the genome of a plant infecting pathogen present in the cell prior to the following manipulations may comprise the steps of: (a) providing a first plant comprising said target sequence, which plant is capable of regenerating; (b) hybridizing said first plant with a second plant transformed with a DNA construct comprising a nucleotide sequence corresponding to the T7 RNA polymerase gene (T7-pol) or a functional equivalent or fragment thereof which sequence carries an NLS sequence, said construct further comprising a plant promoter and a plant terminator sequence operably linked to said T7-pol, a T7 promoter (pT7) or a functional fragment thereof, a targeting sequence downstream to said pT7, and at least one additional promoter sequence operably linked to said targeting sequence and; (c) selecting plants obtained by the hybridization of step (b), wherein the expression of said target sequence is substantially silenced.

In any case, the targeting sequence within the system will substantially corresponds to the target sequence or to a fragment thereof and the target sequence may correspond to: (a) a gene encoding a protein or a peptide product, the silencing of which is desired; (b) a non-coding nucleic acid sequence, which, under normal conditions, promotes the expression of an essential coding sequence; (c) a nucleic acid sequence which corresponds to (a) or to (b) or to a fragment thereof, within the scope of degeneracy of the genetic code; or (d) a nucleic acid sequence which hybridizes with the sequence according to (a), to (b), or to (c) or with fragments thereof, which hybridization is carried out under conditions which allow such hybridization to occur.

Finally, the invention concerns with a method of identifying a nucleic acid of interest within a plant's genome wherein the nucleic acid of interest encodes a pre-defined plant phenotype, which process comprises the steps of: (a) providing a first plant comprising within its genome said nucleic acid of interest; (b) transforming said first plant with a second plant transformed with: (i) a first DNA construct comprising a nucleotide sequence corresponding to the T7 RNA polymerase gene (T7-pol) or a functional equivalent or fragment thereof which sequence carries an NLS sequence, said construct further comprising at least one plant promoter and at least one plant terminator sequence operably lined to said sequence; and with (ii) a second DNA construct comprising a T7 promoter sequence, a random nucleic acid sequence downstream to said T7 promoter, and a 3' non-translated terminator sequence operably linked to said random nucleic acid sequence, said construct optionally further comprising additional regulatory elements operably linked to said nucleic acid of interest, said transformation thus provides a population of transgenic plants; (b) selecting from the population obtained in step (a) transformed plants/plant cells in which the pre-defined phenotype is substantially silenced; and (c) employing said random nucleic acid sequence within the genome of the transformed plants selected in step (c) as a probe in screening genomic DNA and cDNA libraries of said first plant, thereby identifying the gene comprising said random nucleic acid sequence which gene is responsible for said pre-defined phenotype.

Alternatively, the method of identifying a nucleic acid of interest within a plant's genome wherein said nucleic acid of interest encodes a pre-defined plant phenotype, may comprise the steps of: (a) providing a first plant comprising within its genome said nucleic acid of interest; (b) transforming said first plant or with a second plant transformed with a DNA construct comprising a nucleotide sequence corresponding to the T7 RNA polymerase gene (T7-pol) or a functional equivalent or fragment thereof which sequence carries an NLS sequence, said construct further comprising at least one plant promoter sequence and at least one plant terminator sequence operably linked to said T7-pol, said DNA construct further comprising a T7 promoter sequence or a functional fragment thereof, a random nucleic acid sequence downstream to said T7 promoter, and a 3' non-translated terminator sequence operably linked to said random nucleic acid sequence; and (c) selecting from the plants obtained in step (b) those transformed plants in which the pre-defined phenotype is substantially silenced; and (d) employing said random nucleic acid sequences within the genome of the transformed plants selected in step (c) as a probe in screening genomic DNA and cDNA libraries of said first plant, thereby identifying the gene comprising said random nucleic acid sequence, which gene is responsible for said pre-defined phenotype.

Evidently, any further uses of the expression-silencing system, the process for the transformation of a selected cell with said system, the transgenic plant introduced with the system of the invention and the different methods of the invention, are also within the scope of the invention.

The invention will now be described in an illustrative manner and it is to be understood that the terminology which will be used is intended to be in the nature of the words of description rather than of limitation.

Obviously, many modifications and variations of the present invention are possible in light of the above teaching. It is therefore, to be understood that within the scope of the appended claims, the invention may be practiced otherwise than as specifically described.

EXAMPLES

Example 1

General Methodology

DNA sequences were isolated from plants, from bacteriophage T7 and from the virus tobacco mosaic virus (TMV) and propagated in a suitable plasmid (e.g. pBluescript, pCR2.1) in *E. coli* JM109 by a standard procedure [Sambrook J., et al. Molecular Cloning, A Laboratory Manual, Cold Spring Harbor Press (1989); Ausbubel F. M., et al. Current Protocols in Molecular Biology. John Weily & Sons Inc. (1995)]. Alternatively, DNA sequence to be transferred to plants were provided by the binary plasmids (such as the pB1101). The DNA sequences utilized were the plant promoter p35S, the bacteriophage gene for T7 RNA polymerase (T7-pol), the plant terminator NOS, the bacteriophage terminator (T7-terminator), the translation enhancer from TMV ($\Omega$) and the coding sequence of the bacterial gene for $\beta$-glucuronidase (GUS).

Cloning of T7-pol and GUS

Figure 1C:

The gene for T7-pol was 5'-fused with the $\Omega$-translation-enhancer element from TMV and the SV-40 element, NLS, directing protein transport to the nucleus. This construct was placed between a CaMV-35S promoter (p35S) and a NOS terminator and was designated-35S-T7-pol. Two constructs of GUS were prepared, both 5'-fused to $\Omega$: one construct p35S-GUS was placed between p35S and the NOS terminator, and the other (pT7-GUS) between pT7 and, assuming that T7-pol may not recognize plant termination signals, two terminators: the plant NOS terminator and the bacteriophage T7 terminator. All constructs also carried the NPTII gene for Km resistance, and were transferred into the binary plasmids pGA643 and pB1101 [Vardi E., et al. Proc. Natl. Acad. Sci. USA 90:7513–7517 (1993)], which provided border sequences for integration into the plant's genome and cassettes for a selectable marker in plants (kanamycin resistance). FIGS. 1A and 1B show the constructs obtained. FIG. 1C represents a positive control wherein the cassette introduced into the binary plasmid pB1101 carries the GUS coding sequences between p35S and the NOS terminator.

GUS Assay

Gus activity was assayed either histochemically or by fluorometric determination of the production of 4-methylumbelliferone (4-MU) from its substrate 4-methylumbellferyl glucuronide (MUG, sigma) according to the methodology described [Jefferson R. A., Plant Mol. Biol. Rep. 5:387–405 (1987)].

RNA Assay

Figure 3:
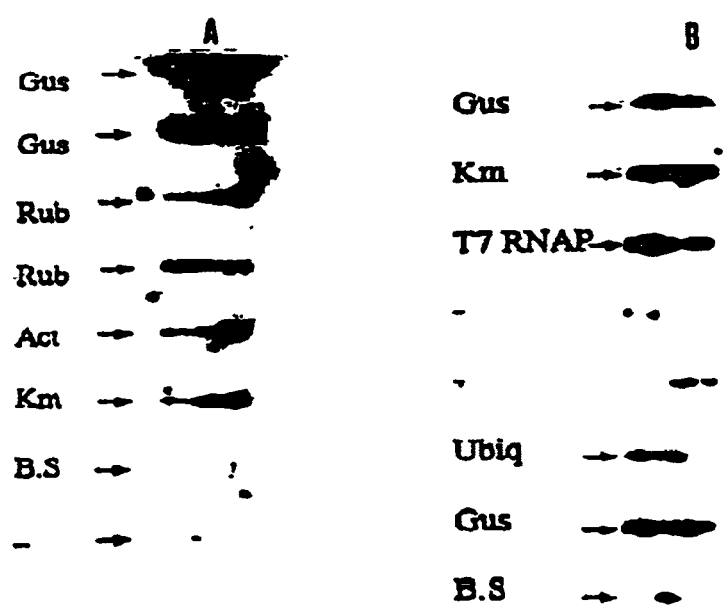

All assays were carried out with p35S-T7-pol/pT7-GUS plants and with 35S-GUS plants as controls. Since the absence of GUS expression could have been attributed to the expression of an inactive T7-pol, or to its inability to move to the nucleus and affect transcription, initial transcription was tested first by nuclear run-on assays. As indicated in FIG. 3, GUS transcripts were driven from p35S as well as from pT7. The level of GUS transcription from pT7 was comparable to that of the expressed T7-pol and NPTII genes (driven by p35S and pNOS, respectively), but higher than the internal control of the ubiquitin gene under its own native promoter. As expected, the control p35S-GUS plants readily transcribed GUS.

RNase-protection assays, however, indicated that while T7-pol-mRNA and actin-mRNA are present in the 35S-T7-pol/pT7-GUS plants, GUS-mRNA is absent. GUS-mRNA and the internal control actin-mRNA were both detected in the control p35S-GUS plants (FIG. 4). Silencing of GUS expression in a plant T7-pol/pT7 system therefore occurs at a post-transcriptional stage.

Nuclear Run-on Assay

The procedure was carried out essentially as described by Cox and Goldberg [Cox K. H., and Glodberg R. H., in Plant Molecular Biology. A Practical Approach (Shaw C. H. Ed) Washington D.C. IRL Press pp 1–35]. Reduction of the starch content was found to be essential for a good preparation. Therefore, plants were stored in the dark for 48 hr prior to nucleic isolation. Nuclei were finally separated on 40–76% percol gradients and stored as 100 µl aliquots at −80° C.

In order to enable quantitative comparisons, relevant plasmids (1 µg per 1000 bp) were boiled and quickly cooled, and the denatured plasmid was slot-blotted onto a nitrocellulose membrane. A regular Southern-type procedure was then performed with the nuclear RNA preparation as a probe.

RNase Protection Assay

GUS mRNA electrophoresed to about the same position as the 18S rRNA. To avoid background problems, RNase protection was therefore preferred to Northern-blot hybridization.

RNase protection assays were carried out essentially according to the manufacturer's protocol (Ribonuclease Protection Kit Ambion). Three probes were prepared for the RNase protection assays: An internal control actin probe (474 bases) was made by PCR amplification of a segment of the actin cDNA between bases 4282–4756 from tobacco DNA (GenBank #X63603). The amplified product was cloned into the plasmid Bluescript KS (Stratagene). The antisense probe was transcribed from the T3 promoter of the linearized recombinant plasmid (BamH1). The GUS probe was prepared by cleaving our an XbaI-EcoR1 fragment from a GUS carrying plasmid (pBI221, Clonetech) and subcloning it into the plasmid Bluescript. A 760 bp antisense probe was prepared by transcribing the MluI-linearized plasmid from the T3 promoter. The probe for T7-pol was a BamH1-EcoR1 fragments subcloned into Bluescript from Tabor and Richardson's plasmid pGPI-2. The antisense probe (240 bp) was transcribed from the T7 promoter of the NdeI-linearized plasmid.

Example 2

Plant Transformation and Silencing of GUS Expression

*Agrobacterium tumefaciens* carrying a compatible disarmed Ti plasmid (e.g. pEHA101) was transformed with one of the engineered binary plasmids by triparental mating [An G., Methods Enzymol. 153:292–305 (1987)], or by electroporation [Li-Chin-Ho et al. Plant Physiology and Biochemistry 35:959–968 (1997)] with GenePulser II (performed according to the manufacturer's instructions, Biorad).

Agrobarterium-mediated transformation was carried out, and homozygous plants were selected at the R2 stage as described previously [Vardi E., et al. (1993) ibid.]. In particular, tobacco and tomato leaf discs were inoculated with the transformed *A. tumefaciens* according to standard procedure [An G. (1987)ibid.]. Agro-inoculated leaf discs were placed on the following medium: MS salts (4.71 gr/L) [Murashige T. and Skoog F. Physiol. Plant. 15:485–497 (1962)], sucrose (20 gr/L), maniol (10 gr/L), Nobel Agar (10 gr/L), seatin (2 mg/L), LAA (indole acetic acid 0.1 Gr/L), pH 5.8. After 48 hrs in this medium, the leaf discs were transferred into a fresh medium further containing kanamycin (300 µg/ml) and carbenicillin (300 µg/ml) which was replaced every 10 days. Callus developed from the leaf discs (20–30 days from Agro-inoculation) was transferred to the same initial medium however containing 400 µg/ml kanamycin. Shoots developing from the callus were transferred individually for root development to a medium containing: MS salts (4.71 g/L), sucrose (30 gr/L), Nobel Agar (10 gr/L). Rooted shoots were then potted and transferred to the greenhouse to grow into mature flowering plants.

As an alternative procedure, plants may be introduced with the relevant vectors also by biolistic methods [Bionard protocols] by bombarding beads coated with the pertinent DNA into plant tissues.

As an alternative to the selection of the transformed plants using a selection marker, efficient selection may be obtained based on PGR identification of the transgene or by histochemical assays for GUS expression, as an alternative or in addition to the selectable marker.

Figure 2:
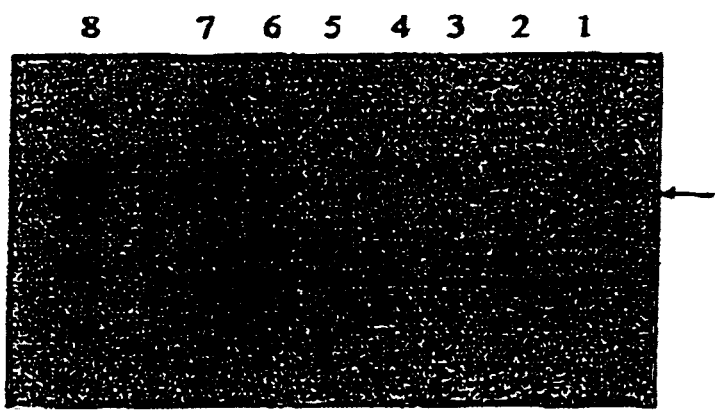
FIG. 2 Western blot analysis for the expression of T7 RNA polymerase.

Plants transformed with the construct shown in FIG. 1A, which were capable of expressing (transcription and translation) GUS, were hybridized with plants transformed with the cassette comprising pT7, Ω, GUS and two terminators (FIG. 1B). The resultant double-transformed plant expressed T7-pol (FIG. 2), transcribed GUS (FIG. 3) but did not produce GUS mRNA (FIG. 4) and thus was unable to express GUS protein (Table 2), which exhibits the silencing of the expression of GUS at the post-transcriptional level. Importantly, the expression of GUS was silenced in all the resulting transgenic plants.

Example 3

Preparation of Progeny Silenced Plants via Pollination (Silencing in Trans)

Transgenic R0 tobacco plants carrying the p35S-RNA-pol construct were crossed with similar plants carrying the pT7-GUS construct (see FIG. 1 for a diagram of the constructs). The hybrid plants were self-pollinated and progeny were selected for several generations. At all stages plants were PCR-analyzed for both T7-pol and GUS, and only plants carrying both genes were selected. Then, a double transformed 35S-T7-pol/pT7-GUS plant was pollinated by an expressing 35S-GUS control plant. Three of the progeny plants out of 18 were found to carry all three genes (35S-T7-pol, pT7-GUS and 35S-GUS) as determined by PCR using a promoter-specific and a gene-specific primers for each case. None of these triple transformed plants exhibited GUS activity either by histochemical staining (data not shown) or by measuring GUS activity in plant's extracts (Table 1). Hence, once the T7-derived silencing machinery was set in motion it was capable of silencing an already active pertinent gene. The evoked silencing mechanism was therefore not a peculiarity of the foreign T7 system but carried relevance to silencing of the gene under a "native" plant promoter.

Many of the 35S-T7-pol/pT7-GUS transgenic plants, belonging to all lines, expressed T7-pol, as indicated by Western-blot analyses. Seedlings of these plants (2,100, belonging to 21 lines) were tested for GUS expression histochemically, or by assaying GUS activity in plant extracts.

T7-driven GUS activity could not be found in these plants. Lack of GUS expression was observed in the double-transformed plants regardless of the level of expression of T7-pol (Table 1). Only in two plants GUS staining was observed in pollen grains (FIG. 2) and callus (data not shown). GUS activity was, however, fully silenced in the leaves of these 2 plants which was corroborated also by nuclear run-on and RNase protection assays.

TABLE 1

GUS enzymatic activity

| The transgenic plant | No. of tested plants | GUS activity (average) nmole 4-MU/h/mg protein |
| --- | --- | --- |
| Non-transformed (SR1) | 5 | 0.7 |
| 35S-GUS | 5 | 272 ± 71 |
| T7-GUS | 5 | 0.8 |
| 35S-T7-pol | 5 | 0.6 |
| 35S-T7-pol/T7-GUS[a] | 5 | 0.7 |
| 35S-T7-pol/T7-GUS/35S-GUS[b] | 3 | 0.6 |

[a]double-transformed plants
[b]triple-transformed plants

Example 4

Silencing of Expressing a Target Gene via Grafting

Transgenic RO tobacco plants carrying the p35S-RNA-pol construct were crossed with similar plants carrying the pT7-GUS construct (FIG. 1). The hybrid plants were self pollinated and progeny were selected for several generations. At all stages plants were PCR-analyzed for both T7-pol and GUS, and only plants carrying the both genes were selected. Then, a scion from an expressing 35S_GUS plant was grafted upon the double-transformed, GUS-silenced plants. Shoots growing from the grafted scions were examined for GUS expression histochemically. Three out of the 6 plants in this experiment were silenced for GUS. Hence, in some cases, once the T7-derived silencing machinery was set in motion, it was capable of signal silencing to an already active pertinent gene across a graft.

Example 5

Conferring Plants with Resistance to a Plant Pathogen (TMV)

Resistance to TMV in plants carrying the expression silencing system of the invention which included a TMV originated sequence (Ω) downstream to pT7 was also examined. Accordingly, several of the double-transformed plants were inoculated with TMV (10 μg/ml in 0.01M phosphate buffer). Seven days post-inoculation, five leaf discs (6 mm in diameter) were cut of randomly from each plant and identically processed for ELISA with antibodies raised against the purified virus. The results presented in Table 1 show that all the double-transformed plant became partially or fully resistant to TMV (Table 2).

These results and the results presented for the silencing of GUS expression clearly indicate that the expression silencing system of the invention may carry a variety of targeting genes, homologous or heterologous, thereby silencing a broad spectrum of genes of interest.

TABLE 2

ELISA readings for TMV in tobacco plants

| Type of plant | Absorbance at 405 nm |
| --- | --- |
| Non-infected | 0.038 |
| Non-transgenic, TMV infected | 0.614 |
| Double transformant 1 | 0.208 |
| Double transformant 2 | 0.022 |
| Double transformant 3 | 0.250 |
| Double transformant 4 | 0.087 |
| Double transformant 5 | 0.015 |
| Triple transformant 1 | 0.045 |
| Triple transformant 2 | 0.008 |
| Triple transformant 3 | 0.042 |

What is claimed is:

1. A method of silencing the expression of a target sequence within the genome of a plant, which method comprises the steps of:
   a) providing a first plant capable of regenerating;
   b) hybridizing said first plant with a second plant double transformed with:
      i) a first DNA construct comprising the T7 RNA polymerase gene (T7-pol) and a NLS sequence, said construct further comprising at least one plant promoter and at least one plant terminator sequence operably linked to said T7-pol; and with
      ii) a second DNA construct comprising a T7 promoter sequence (pT7), a targeting sequence downstream to said pT7 and a 3' non-translated terminator sequence operably linked to said targeting sequence, said construct optionally further comprising additional regulatory elements operably linked to said targeting sequence; and
   c) selecting those plants obtained by the hybridization of step (b), in which the expression of said target sequence is silenced.

2. A method of silencing the expression of a target sequence within the genome of a plant, which method comprises the steps of:
   a) providing a first plant comprising said target sequence, said plant being capable of regenerating;
   b) hybridizing said first plant with a second plant transformed with a DNA construct comprising the T7 RNA polymerase gene (T7-pol), a NLS sequence, a plant promoter and a plant terminator sequence operably linked to said T7-pol, a T7 promoter (pT7), a targeting sequence downstream to said pT7, and at least one additional promoter sequence operably linked to said targeting sequence; and c) selecting those plants obtained by the hybridization of step (b), in which the expression of said target sequence is silenced.

3. A method for silencing the expression of a target gene within a plant cell comprising the steps of:
   a) transforming a plant cell with a first construct comprising the T7 RNA polymerase gene (T7-pol), a NLS sequence, and at least one promoter and at least one terminator sequence operably linked to said T7-pol;
   b) selecting plant cells transformed with said first DNA construct according to step (a);
   c) transforming the selected plant cells obtained in step (b) with a second DNA construct comprising a T7 promoter sequence, a targeting sequence downstream to said T7 promoter, and at least one 3' non-translated terminator sequence operably linked to said targeting sequence, said construct optionally further comprising other additional regulatory elements operably linked to said targeting sequence;
   d) selecting from the plant cells obtained in step (c), cells transformed with said second DNA construct;
   whereby transformation of said plant cell with said first and second DNA constructs renders the expression of said target sequence silenced.

4. A method for silencing the expression of a target gene within a plant cell comprising the steps of:
   a) transforming said plant cell with a DNA construct comprising the T7 RNA polymerase gene (T7-pol) and a NLS sequence, said construct further comprising at least one plant promoter sequence and at least one plant terminator sequence operably linked to said T7 polymerase gene, a T7 promoter sequence (pT7), a targeting sequence downstream to said pT7, and at least one additional terminator sequence operably linked to said targeting sequence, which DNA construct is capable, upon transformation thereof into a plant cell, of rendering the expression of a target sequence in said plant cell silenced; and
   b) selecting plant cells transformed with said DNA construct according to (a) and regenerating said selected cells to provide a differentiated flowering plant.

5. A method for silencing the expression of a target gene within a plant comprising the steps of:
   a) transforming a first population of plant cells with a first construct comprising the T7 RNA polymerase gene (T7-pol) and a NLS sequence, and further comprising at least one plant promoter and at least one plant terminator sequence operably linked to said T7-pol;
   b) selecting the cells obtained in step (a), cells transformed with said first DNA construct, and regenerating said selected cells to provide a differentiated flowering plant;
   c) transforming a second population of plant cells with a second DNA construct comprising a T7 promoter sequence, a targeting sequence downstream to said T7 promoter, and at least one 3' non-translated terminator sequence operably linked to said targeting sequence, said construct optionally further comprising other additional regulatory elements operably linked to said targeting sequence;
   d) selecting from the plant cells obtained in step (c), cells transformed with said second DNA construct, and regenerating said selected cells to provide a differentiated flowering plant; and
   e) hybridizing a first plant transformed with said first DNA construct as obtained in (b), with a second plant transformed with said second DNA construct as obtained in (d), thereby providing a double-transformed plant in which the expression of said target gene is silenced.

6. A method of silencing the expression of a target sequence within the genome of a plant, wherein said target sequence is one of:
   I) a gene which encodes a plant protein or peptide product,
   II) a transcribed non-coding nucleic acid sequence, or
   III) a nucleic acid sequence which is a fragment of (I) or (II),
   which method comprises the steps of:
   a) providing a first plant capable of regenerating;
   b) hybridizing said first plant with a second plant double transformed with:
      i) a first DNA construct comprising the T7 RNA polymerase gene (T7-pol) and a NLS sequence, said construct further comprising a pass plant promoter and a plant terminator sequence, wherein said plant terminator sequence is the NOS terminator or the β-1,3-gluconase terminator, operably linked to said T7-pol; and with
      ii) a second DNA construct comprising a T7 promoter sequence (pT7), a targeting sequence downstream to said pT7 and a 3' non-translated terminator sequence operably linked to said targeting sequence, wherein said pT7 is the promoter region of the bacteriophage T7 capable of initiating transcription of said downstream targeting sequence and the terminator is the NOS terminator operably linked to said targeting sequence, said construct optionally further comprising additional regulatory elements operably linked to said targeting sequence, wherein said targeting sequence is identical to at least part of a target expressed sequence or is identical to at least part of a non-coding sequence which is a regulatory element sequence and is transcribed; and
   c) selecting those plants obtained by the hybridization of step (b), wherein expression in the progeny of the cross resulting from step (b) is silenced by causing the disappearance of the RNA transcripts of said target sequence.

7. A method of silencing the expression of a target sequence within the genome of a plant, wherein said target sequence is one of:
   I) a gene which encodes a plant protein or peptide product,
   II) a transcribed non-coding nucleic acid sequence, or
   III) a nucleic acid sequence which is a fragment of (I) or (II),
   which method comprises the steps of:
   a) providing a first plant comprising said target sequence, said plant being capable of regenerating;
   b) hybridizing said first plant with a second plant transformed with a DNA construct comprising the T7 RNA polymerase gene (T7-pol), a NLS sequence and further comprising a p35S plant promoter and a plant terminator sequence, wherein said plant terminator sequence is the NOS terminator or the β-1,3-gluconase terminator, operably linked to said T7-pol, a T7 promoter (pT7), a targeting sequence downstream to said pT7, and at least one additional promoter sequence operably linked to said targeting sequence, wherein said targeting sequence is identical to at least part of a target expressed sequence or is identical to at least part of a non-coding sequence which is a regulatory element sequence and is transcribed; and c) selecting those plants obtained by the hybridization of step (b), wherein expression in the progeny of the cross resulting from step (b) is silenced by causing the disappearance of the RNA transcripts of said target sequence.

8. A method for silencing the expression of a target gene within a plant cell, wherein said target sequence is one of:
I) a gene which encodes a plant protein or peptide product,
II) a transcribed non-coding nucleic acid sequence, or
III) a nucleic acid sequence which is a fragment of (I) or (II),
comprising the steps of:
a) transforming a plant cell with a first construct comprising the T7 RNA polymerase gene (T7-pol), a NLS sequence, further comprising a p35S plant promoter and a plant terminator sequence, wherein said plant terminator sequence is the NOS terminator or the β-1,3-gluconase terminator, operably linked to said T7-pol;
b) selecting plant cells transformed with said first DNA construct according to step (a);
c) transforming the selected plant cells obtained in step (b) with a second DNA construct comprising a T7 promoter sequence, a targeting sequence downstream to said T7 promoter, and at least one 3' non-translated terminator sequence operably linked to said targeting sequence, wherein said pT7 is the promoter region of the bacteriophage T7 capable of initiating transcription of said downstream targeting sequence and the terminator is the NOS terminator operably linked to said targeting sequence, said construct optionally further comprising other additional regulatory elements operably linked to said targeting sequence, and wherein said targeting sequence is identical to at least part of a target expressed sequence or is identical to at least part of a non-coding sequence which is a regulatory element sequence and is transcribed;
d) selecting from the plant cells obtained in step (c), cells transformed with said second DNA construct, whereby transformation of said plant cell with said first and second DNA constructs renders the expression of the target sequence in said cell, in a tissue, organ, or plant regenerated from said cell, or in a progeny thereof silenced by causing the disappearance of the RNA transcripts of said target sequence.

9. A method for silencing the expression of a target gene within a plant cell, wherein said target sequence is one of:
I) a gene which encodes a plant protein or peptide product,
II) a transcribed non-coding nucleic acid sequence, or
III) a nucleic acid sequence which is a fragment of (I) or (II),
comprising the steps of:
a) transforming said plant cell with a DNA construct comprising the T7 RNA polymerase gene (T7-pol) and a NLS sequence, said construct further comprising a p35S plant promoter and a plant terminator sequence, wherein said plant terminator sequence is the NOS terminator or the β-1,3-gluconase terminator, operably linked to said T7-pol gene, a T7 promoter sequence (pT7), a targeting sequence downstream to said pT7, wherein said pT7 is the promoter region of the bacteriophage T7 capable of initiating transcription of said downstream targeting sequence and the terminator is the NOS terminator operably linked to said targeting sequence, and at least one additional terminator sequence operably linked to said targeting sequence, and wherein said targeting sequence is identical to at least part of a target expressed sequence or is identical to at least part of a non-coding sequence which is a regulatory element sequence and is transcribed, wherein upon introduction of said DNA construct into a cell or plant, the expression of the target sequence in said cell, in a tissue, organ, or plant regenerated from said cell, or in a progeny thereof, is silenced by causing the disappearance of the RNA transcripts of said target sequence; and b) selecting plant cells transformed with said DNA construct according to (a) and regenerating said selected cells to provide a differentiated flowering plant.

10. A method for silencing the expression of a target gene within a plant, wherein said target sequence is one of:
I) a gene which encodes a plant protein or peptide product,
II) a transcribed non-coding nucleic acid sequence, or
III) a nucleic acid sequence which is a fragment of (I) or (II),
comprising the steps of:
a) transforming a first population of plant cells with a first construct comprising the T7 RNA polymerase gene (T7-pol) and a NLS sequence, and further comprising a p35S plant promoter and a plant terminator sequence, wherein said plant terminator sequence is the NOS terminator or the β-1,3-gluconase terminator, operably linked to said T7-pol;
b) selecting the cells obtained in step (a), cells transformed with said first DNA construct, and regenerating said selected cells to provide a differentiated flowering plant;
c) transforming a second population of plant cells with a second DNA construct comprising a T7 promoter sequence, a targeting sequence downstream to said T7 promoter and at least one 3' non-translated terminator sequence operably linked to said targeting sequence, wherein said pT7 is the promoter region of the bacteriophage T7 capable of initiating transcription of said downstream targeting sequence and the terminator is the NOS terminator operably linked to said targeting sequence, and wherein said targeting sequence is identical to at least part of a target expressed sequence or is identical to at least part of a non-coding sequence which is a regulatory element sequence and is transcribed, said construct optionally further comprising other additional regulatory elements operably linked to said targeting sequence; and
d) selecting from the plant cells obtained to step (c), cells transformed with said second DNA construct, and regenerating said selected cells to provide a differentiated flowering plant;
e) hybridizing a first plant transformed with said first DNA construct as obtained in (b), with a second plant transformed with said second DNA construct as obtained in (d), thereby providing a double-transformed plant in which the expression of said target gene is silenced by causing the disappearance of the RNA transcripts of said target sequence.

* * * * *